US009498614B2

(12) United States Patent
Alpert (10) Patent No.: US 9,498,614 B2
(45) Date of Patent: *Nov. 22, 2016

(54) NEEDLELESS VALVE INFECTION PREVENTION AND PRE-OPENING DEVICE

(71) Applicant: CareFusion 303, Inc., San Diego, CA (US)

(72) Inventor: Robert S. Alpert, Escondido, CA (US)

(73) Assignee: CAREFUSION 303, INC., San Diego, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 14/275,810

(22) Filed: May 12, 2014

(65) Prior Publication Data

US 2014/0249512 A1    Sep. 4, 2014

Related U.S. Application Data

(63) Continuation of application No. 12/841,959, filed on Jul. 22, 2010, now Pat. No. 8,721,627.

(51) Int. Cl.
| A61M 25/16 | (2006.01) |
|---|---|
| A61M 25/18 | (2006.01) |
| A61M 39/00 | (2006.01) |
| A61M 39/10 | (2006.01) |
| A61M 39/16 | (2006.01) |
| A61M 39/18 | (2006.01) |
| A61M 39/20 | (2006.01) |

(52) U.S. Cl.
CPC ............ *A61M 39/165* (2013.01); *A61M 39/16* (2013.01); *A61M 39/162* (2013.01); *A61M 39/18* (2013.01); *A61M 39/20* (2013.01); *A61M 2039/1072* (2013.01); *A61M 2039/1077* (2013.01); *A61M 2205/0205* (2013.01)

(58) Field of Classification Search
CPC ............ A61M 2039/1072; A61M 2039/1077; A61M 2205/0205; A61M 39/16; A61M 39/162; A61M 39/165; A61M 39/18; A61M 39/20
See application file for complete search history.

(56) References Cited

U.S. PATENT DOCUMENTS

| 5,190,534 | A | 3/1993 | Kendell |
|---|---|---|---|
| 7,632,261 | B2 | 12/2009 | Zinger et al. |
| 2009/0062766 | A1 | 3/2009 | Howlett et al. |
| 2009/0205151 | A1 | 8/2009 | Fisher et al. |
| 2010/0003067 | A1 | 1/2010 | Shaw et al. |
| 2010/0047123 | A1 | 2/2010 | Solomon et al. |
| 2010/0050351 | A1 | 3/2010 | Colantonio et al. |
| 2010/0172794 | A1 | 7/2010 | Ferlic et al. |
| 2011/0054440 | A1 | 3/2011 | Lewis |

FOREIGN PATENT DOCUMENTS

| WO | WO-2006019782 A2 | 2/2006 |
|---|---|---|
| WO | WO-2009002474 A1 | 12/2008 |
| WO | WO-2010115005 A1 | 10/2010 |

OTHER PUBLICATIONS

Supplementary European Search Report in European Patent Application No. 11809989.4/Patent No. 2595692 dated Jul. 18, 2014.

*Primary Examiner* — Rebecca E Eisenberg
(74) *Attorney, Agent, or Firm* — McDermott Will & Emery LLP (57) ABSTRACT

A disinfecting and pre-opening device is disclosed for use with a female needleless connector. The disinfecting and pre-opening device includes a housing comprising a chamber having a distal opening and configured to fit over the female needleless connector, and an elongated finger attached to the housing and disposed within the chamber such that the elongated finger opens the fluid path through the female needleless connector when the distal opening of the disinfecting and pre-opening device is placed proximally adjacent to the septum and the disinfecting and pre-opening device is advanced in the distal direction.

20 Claims, 10 Drawing Sheets

NEEDLELESS VALVE INFECTION PREVENTION AND PRE-OPENING DEVICE

FIELD

This application is a continuation of U.S. application Ser. No. 12/841,959, filed Jul. 22, 2010, entitled, "NEEDLELESS VALVE INFECTION PREVENTION AND PRE-OPENING DEVICE," the disclosure of which is incorporated herein by reference in its entirety.

BACKGROUND

Many healthcare facilities have converted to needleless intravenous (IV) infusion systems to reduce the risk of injury to the healthcare provider. The infusion sets that are used as part of a needleless infusion system frequently have access ports so that additional medications can be administered without disconnecting the tubing from the IV pump or IV fluid container. One such needleless system uses Luer fittings to connect fluid components together, with the female Luer connector that may incorporate an elastomeric septum having a slit or a piston. When a syringe or other fluid container that is fitted with a male Luer connector is mated to the female Luer connector of the access port, the male Luer tip penetrates through the slit in the septum or displaces the piston to establish a fluid path between the connectors.

Needleless connectors in an IV system must be sterile prior to the mating of the two connectors to prevent bacteria or other microorganisms from being carried by the IV fluid into the bloodstream of the patient. While the access port is sterile when removed from its package, it is exposed to the open air while in use and can possibly be contaminated shortly after it is removed from the package. It is a common protocol to sterilize the surface of the septum of the access port by wiping the septum with a disinfectant such as isopropyl alcohol immediately prior to mating a male Luer connector to the access port. This requires the healthcare provider to have alcohol wipes on hand and, if they do not have any wipes or swabs available when they are about to connect a fluid container to the access port, they must stop and return to the supply cabinet to gather more alcohol wipes. This takes up valuable time and creates a risk of this sterilization step being skipped.

Healthcare providers occasionally experience difficulty in connecting a male Luer fitting to a female Luer connector having a pre-slit septum. The tip of the male Luer fitting may not entirely penetrate the slit and the septum deforms without creating a fluid path. In such cases, the connectors must be separated and reconnected, which creates an opportunity for contamination of the connector surfaces and is not clinically recommended. In some cases, the slit will not fully open and the healthcare provider must replace the infusion set having the failed access port, which consumes the healthcare provider's time and may cause discomfort for the patient as well as present additional risk of infection or sympathetic flow.

Accordingly, there is a need for a device and method that increases the probabilities that an exposed surface of a female Luer connector is disinfected prior to mating connectors and that the pre-slit septum will properly mate with a male Luer fitting.

SUMMARY

The disclosed device enables healthcare providers to sterilize the external surface of a pre-slit septum in a female Luer connector and pre-opens the slit to ensure that a proper fluid path is established during the first access when a male Luer connector is mated to the female Luer connector.

A disinfecting and pre-opening device is disclosed for use with a female needleless connector. The disinfecting and pre-opening device includes a housing comprising a chamber having a distal opening and configured to fit over the female needleless connector, and an elongated finger attached to the housing and disposed within the chamber such that the elongated finger opens the fluid path through the female needleless connector when the distal opening of the disinfecting and pre-opening device is placed proximally adjacent to the septum and the disinfecting and pre-opening device is advanced in the distal direction.

In another embodiment, a disinfecting and pre-opening system for use with a female needleless connector is disclosed. The disinfecting and pre-opening system includes a fluid delivery appliance having a male needleless connector; and a disinfecting and pre-opening device removably coupled to the male needleless connector of the fluid delivery appliance. The disinfecting and pre-opening device includes a housing comprising a chamber configured to fit over the female needleless connector, a disinfectant disposed within the chamber, and an elongated finger attached to the housing and disposed within the chamber such that the elongated finger opens the fluid path through the female needleless connector when the distal opening of the disinfecting and pre-opening device is placed proximally adjacent to the septum and the disinfecting and pre-opening device is advanced in the distal direction.

In another embodiment, a method of disinfecting and pre-opening a female needleless connector, and connecting a fluid delivery appliance having a male needleless connector to the female needleless connector is disclosed. The method includes the steps of removing a portion of a lid that is removably sealed across a distal opening of a chamber of a disinfecting and pre-opening device, wherein the chamber is configured to fit over the female needleless connector and the chamber contains a disinfectant and a finger, placing the distal opening of the disinfecting and pre-opening device proximally adjacent to the septum of the female needleless connector and advancing the disinfecting and pre opening device in the distal direction until the disinfectant contacts the surface of the septum and the finger opens the fluid path through the female needleless connector, removing the disinfecting and pre-opening device from the female needleless connector, and mating the male needleless connector of the fluid delivery appliance to the female needleless connector.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Bloodstream infections acquired while undergoing medical treatment present a serious risk to patients. The connectors in an infusion system that are exposed to the open air for a period of time prior to a connection being made from a fluid source are a potential source of infection, as any bacteria that have accumulated on the surface of the connector may be carried directly into the blood stream by the fluid passing through the connector. While it is a common protocol to sterilize the external surface of the connector prior with an alcohol wipe prior to connecting a fluid source, this step may be ineffective if performed incorrectly or may be skipped altogether in some circumstances. One approach to ensuring that a connector is sterilized prior to use is to provide a convenient device that enables the healthcare provider to easily complete an effective sterilization.

Failure to be able to mate a male Luer fitting to a female Luer access port having a pre-slit septum that is part of an IV set may require either disconnection and reconnection of the connector fittings or possibly replacement of the entire IV set, both of which present an additional risk of infection to the patient. The causes of a pre-slit septum failing to accept a male Luer fitting may include cross-linking of elastomeric components, such as the two sides of a slit in a elastomeric septum or between a piston and the surrounding housing, during the sterilization process during manufacture, failure of the factory-applied lubricant to satisfactorily penetrate the slit of the septum or between the piston and housing, and roughness of the surface of the male Luer tip of the mating connector. One approach to eliminating these sources of failure is to pre-open the fluid path of the female needleless connector during disinfection and prior to connecting a fluid delivery appliance such as a syringe or IV tubing connected to an IV fluid bag. This breaks any cross-link bonds between portions of the female needleless connector and carries the lubricant that is on the surface down into the slit or between the piston and housing.

Certain exemplary embodiments of the present disclosure include a device that disinfects and pre-opens a female needleless connector. The device may be provided as a separate item or as an accessory that can be attached to a male Luer fitting of a fluid delivery appliance.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
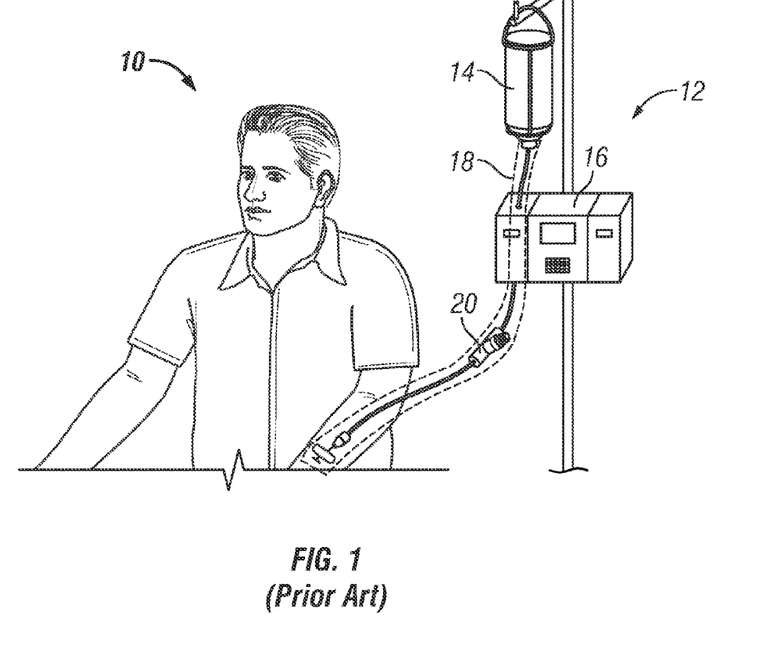
FIG. 1 illustrates an example prior art IV infusion system.

FIG. 1 illustrates an example prior art IV infusion system 12. The infusion system 12 incorporates a flexible IV bag 14 connected through IV set 18, which includes the lines and fittings within the dashed line, to an infusion pump 16 and then to a patient 10. The fluid in the IV bag 14 may be a saline solution or a solution containing one or more medications. If an additional medication must be administered, such as a medication to alleviate pain, it is undesirable to either disconnect any portion of the current IV set 18 or to start a new infusion line as both present an additional risk of infection. The example infusion set 18 includes an access port 20 having a needleless connector so that the additional medication may be administered through the existing IV set 18 without disconnecting any portion of the IV set 18.

Figure 2:
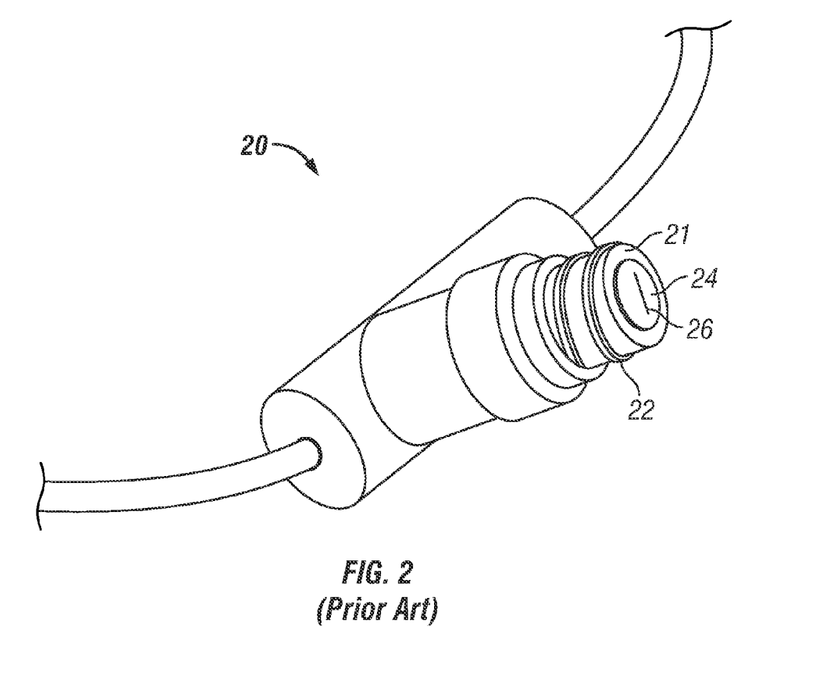
FIG. 2 is an enlarged view of a prior art female Luer access port of FIG. 1 having a pre-slit septum.

FIG. 2 is an enlarged view of a prior art female Luer access port 20 of FIG. 1 having a pre-slit septum. The access port 20 has a housing 21 with external threads 22 so that a male Luer fitting (not shown) may be securely and removably connected to the access port 20. The septum 24 is, in this example, an elastomeric plug that is mounted flush with the external surface at one end of the access port 20 to eliminate features that are difficult to sterilize. The septum 24 has a central slit 26 through the thickness of the septum 24. The slit 26 is normally closed and fluid-tight when not connected to another Luer connector. Other configurations of access slits, such as an "X" shaped cross-cut, as well as other types of needleless connectors incorporating other types of seals, such as pistons, are also used in practice.

Figure 3A:
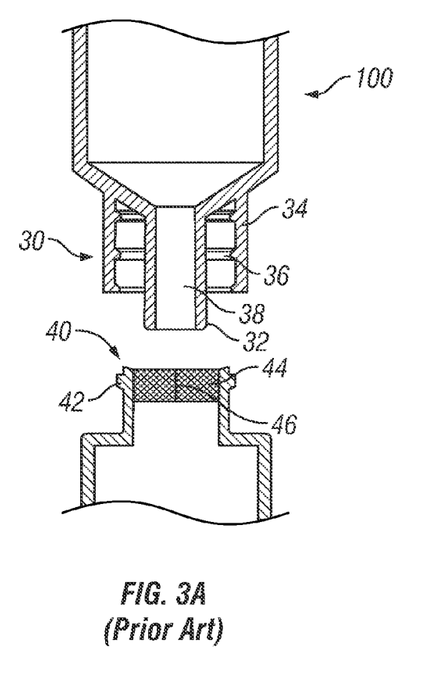
FIGS. 3A-3B illustrate a prior art process of connecting a male Luer connector to a female Luer connector having a pre-slit septum.
Figure 3B:
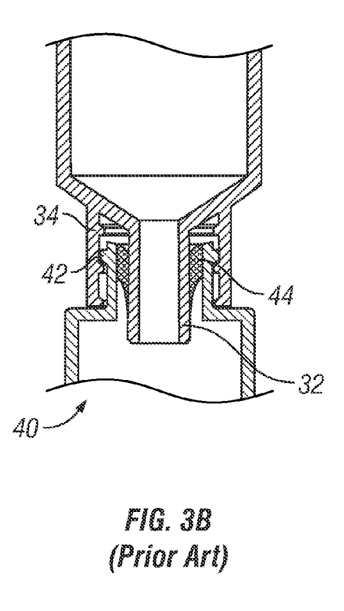

FIGS. 3A and 3B are cross-sectional views depicting a male Luer connector 30 and a female Luer connector 40 before and after making a needleless Luer connection, respectively. In the illustrated example, the male Luer connector 30 includes a housing 34 having a first Luer screw thread 36 formed therein. The male Luer connector 30 further includes a male Luer tip 32 having a cannula 38. In the illustrated example, the male Luer connector 30 is a part of a syringe 100, but in other embodiments, the male Luer connector may be connected to a fluid source (e.g., an IV bag), IV tubing, or other fluid delivery appliance. The female Luer connector 40 has an elastomeric septum 44 with a slit 46, shown as a line through the thickness of septum 44 in this cross-section view. The housing of connector 40 incorporates threads 42 that will be engaged by threaded sleeve 34 of connector 30. FIG. 3B illustrates the configuration of a successfully mated pair of Luer connectors 30 and 40, wherein the male Luer tip 32 has penetrated through slit 46 and the threaded sleeve 34 is engaged with the threads 42 of the female Luer connector. In this configuration, there is a fluid path from connector 30 to connector 40 through the male Luer tip 32.

Figure 3C:
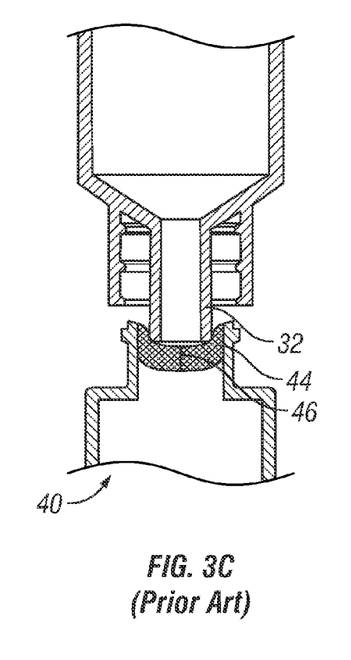
FIG. 3C illustrates one possible failure mode in a prior art process of connecting a male Luer connector to a female Luer connector having a pre-slit septum.

FIG. 3C illustrates one possible failure mode in connecting a male Luer connector 30 to a female Luer connector 40. The male Luer tip 32 has not penetrated slit 46 and there is no fluid path from connector 30 to connector 40. This failure may be due to the elastomeric material of septum 44 having cross-linked across slit 46 during the sterilization process during manufacture and the blunt shape of male Luer tip 32 is not effective in breaking this cross-linked bond. Another possible cause of this failure may be that the material of male Luer tip 32 is not sliding when in contact with the surface of septum 44 due to a lack of lubricant or the roughness of the male Luer tip 32.

Figure 3D:
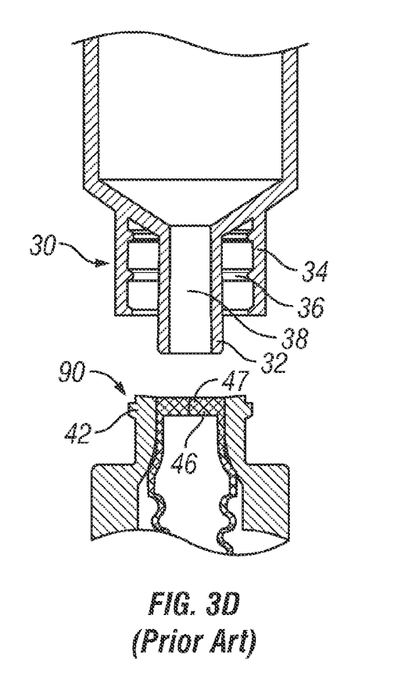
FIGS. 3D-3E illustrate a prior art process of connecting a male Luer connector to a female Luer connector having a piston with a pre-cut slit.
Figure 3E:
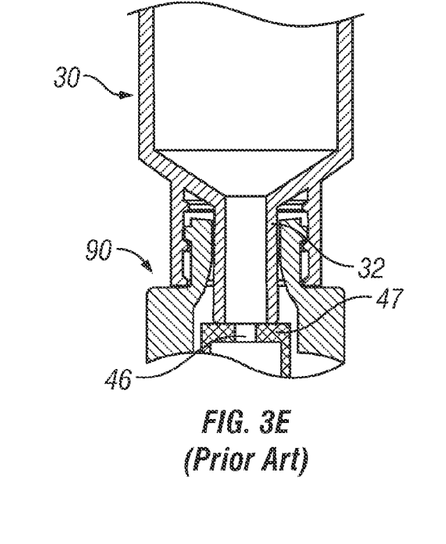

FIGS. 3D-3E illustrate a prior art process of connecting a male Luer connector 30 to a female Luer connector 90 having a piston 47 with a pre-cut slit 46. FIG. 3D illustrates a portion of the piston 47 which has a flat upper surface that is flush with the end of body 41 of FIG. 3A and a collapsible body within the female Luer connector 90. FIG. 3E illustrates the configuration of a successfully mated pair of Luer connectors 30 and 90, wherein the male Luer tip 32 has pushed the piston 47 into the body of Luer connector 90, whereupon slit 46 opens, and the threaded sleeve 34 is engaged with the threads 42 of the female Luer connector. In this configuration, there is a fluid path from connector 30 to connector 90 through the male Luer tip 32 and slit 46.

In other configurations of female Luer connectors having pistons, the piston may not have a slit 46 and may form a fluid path by deformation of the piston 47 that opens a fluid path between the side wall of male Luer tip 32 and piston 47. In other configurations, the surface of piston 47 may be shaped so as to provide gaps between male Luer tip 32 and the surface of piston 47 over a portion of the circumference of male Luer tip 32.

Figure 3F:
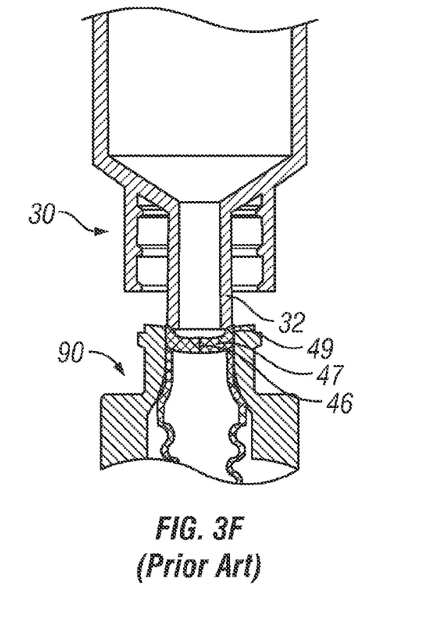
FIG. 3F illustrates one possible failure mode in a prior art process of connecting a male Luer connector to a female Luer connector having a piston with a pre-cut slit.

FIG. 3F illustrates one possible failure mode in a prior art process of connecting a male Luer connector to a female Luer connector 90 having a piston 47 with a pre-cut slit 46. In this example, piston 47 has bonded to the housing 41, preventing the piston from moving down into the wider region 45 where slit 46 opens. Slit 46 may also be cross-linked, further obstructing the flow path through the female Luer connector 90.

Figure 4A:
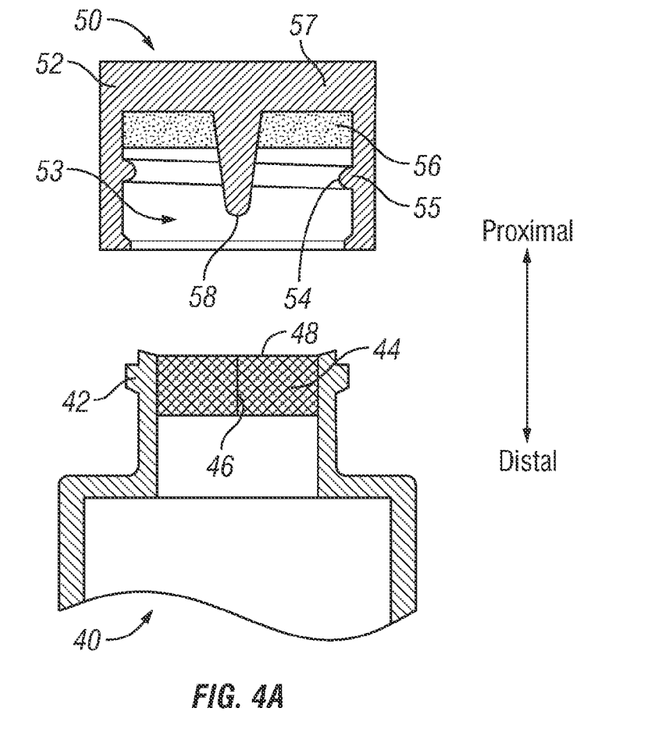
FIGS. 4A-4D illustrate a disinfecting and pre-opening device according to certain embodiments of the present disclosure.

FIGS. 4A-4D illustrate a disinfecting and pre-opening device 50 according to certain embodiments of the present disclosure. As shown in FIG. 4A, device 50 is a separate item that is applied to the female Luer connector 40 prior to mating the male Luer connector 30 of FIG. 3A. The disinfecting and pre-opening device 50 comprises a housing 52 having a chamber 53 of a diameter sufficient to encompass the width of the female Luer connector 40. The chamber 53 is formed from a circumferential sidewall 55 and a proximal wall 57. Threads 54 are formed on the inner wall of circumferential sidewall 55 and are of the proper size and shape to engage the threads 42 of the female Luer connector 40. Within the chamber 53 is a matrix 56 that is configured to retain a quantity of a disinfectant fluid such as, for example and without limitation, isopropyl alcohol or chlorhexadine. The matrix 56 can be any fluid-absorbing material such as, for example and without limitation, polyester, polyvinyl acetate, polyurethane, or cotton, and may be formed into a woven or nonwoven pad or a foam. In certain embodiments, the matrix 56 is at least partially attached (e.g., glued) to an inside surface of the chamber 53 to prevent movement of the matrix 56 during use. Device 50 also incorporates a central finger 58 sized such that the tip will fully penetrate the septum of most female Luer connectors. In this example, finger 58 has a rounded tip and a tapered shaft and a height that is less than the height of housing 52 such that finger 58 will not contact a surface placed across the distal opening of housing 52 thereby avoiding contamination. The female Luer connector 40 has a septum 44 mounted to the proximal end of body 41, septum 44 having a proximal surface 48 and a slit 46, shown in this view as dividing the septum 44 into two pieces although septum 44 is a single element when viewed in perpendicular directions. Surface 48 may have a coating of lubricant (not shown) that was applied at the time of manufacture. Threads 42 are formed on the external wall of body 41 and conform, in this example, to the generally accepted Luer dimensions.

Figure 4B:
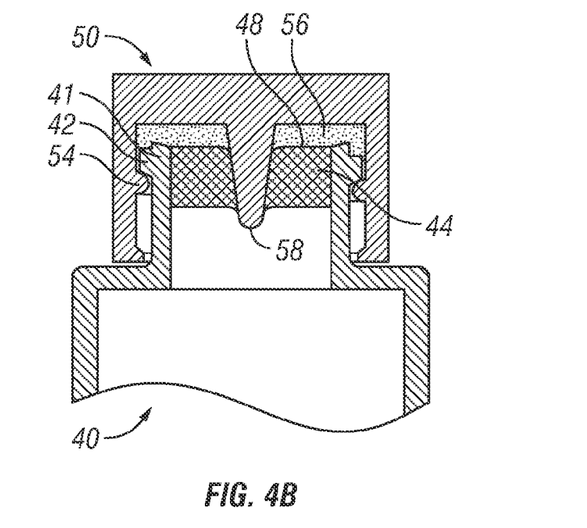

FIG. 4B illustrates the position of device 50 after it has been mated with female Luer connector 40 and rotated until the matrix 56 is seated against the surface 48 of septum 44. Contact with or compression of matrix 56 may release a portion of the liquid disinfectant to wet the surface 48 as well as the portions of the body 41 adjacent to surface 48. At the same time, finger 58 has penetrated slit 46, carrying lubricant from surface 48 into slit 46. Additionally, disinfectant released from matrix 56 may infiltrate the slit 46 along the side of finger 58. The rotation of the device 50 as the matrix 56 comes into contact with surface 48 may additionally provide a scrubbing action that may assist in the cleaning and disinfection of surface 48.

Figure 4C:
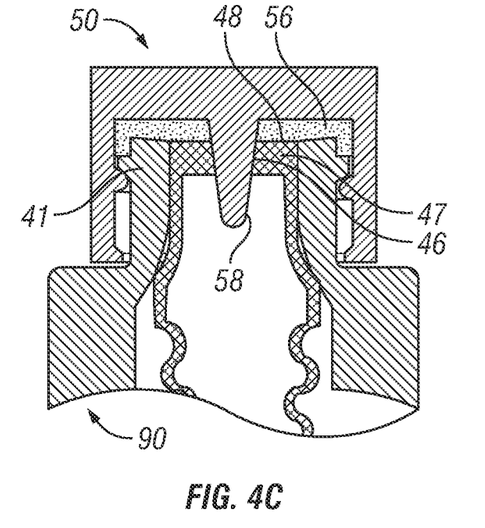

FIG. 4C illustrates the position of device 50 after it has been mated with female Luer connector 90 and rotated until the matrix 56 is seated against the surface 48 of piston 47. Contact with or compression of matrix 56 may release a portion of the liquid disinfectant to wet the surface 48 as well as the portions of the body 41 adjacent to surface 48. At the same time, finger 58 has displaced piston 47, allowing lubricant to coat the surface of body 41 formerly in contact with the side of piston 47, and penetrated slit 46, carrying lubricant from surface 48 into slit 46. Additionally, disinfectant released from matrix 56 may infiltrate the slit 46 along the side of finger 58.

Figure 4D:
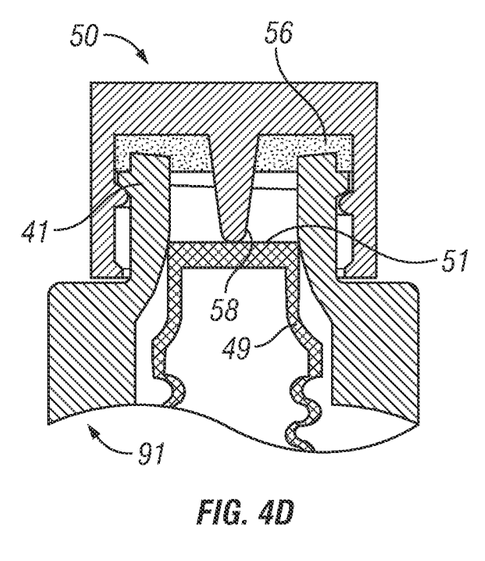

FIG. 4D illustrates the position of device 50 after it has been mated with a female Luer connector 91 that comprises a piston 49 that does not have a slit, wherein the flow path through the female Luer connector 91 is between housing 41 and the outside of piston 49. Finger 58 has displaced piston 49 to break any cross-links between the piston 49 and the housing 41 and open the fluid path through female Luer connector 91. Disinfectant released from matrix 56 may flow down and onto the surface 51 of piston 49, or disinfection of surface 51 may be performed as a separate operation.

Figure 5A:
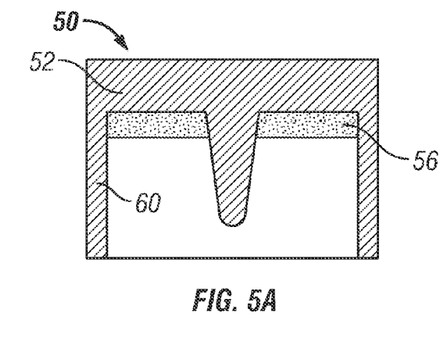
FIGS. 5A-5D illustrate a disinfecting and pre-opening device according to certain other embodiments of the present disclosure.
Figure 5B:
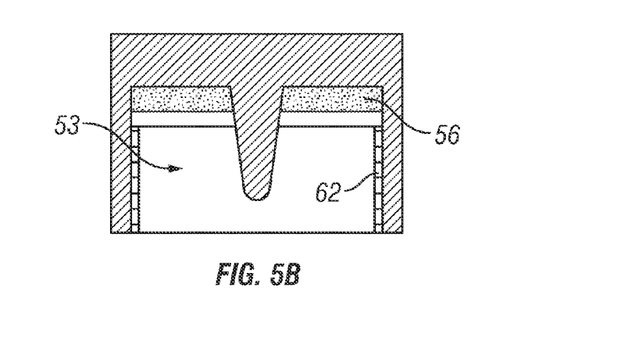
Figure 5C:
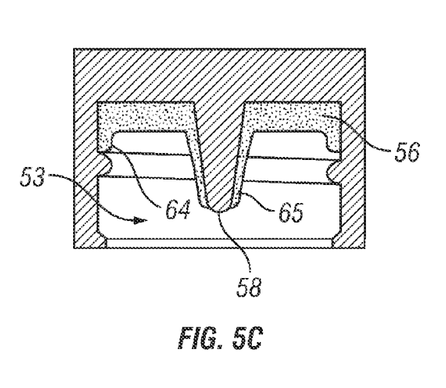
Figure 5D:
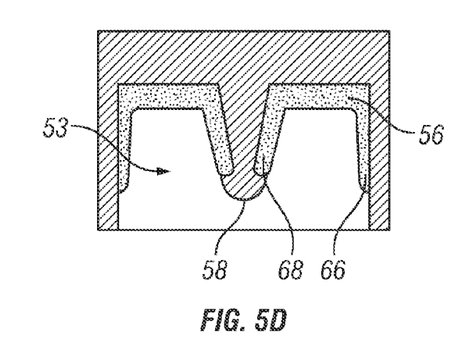

FIGS. 5A-5D illustrate configurations of a disinfecting and pre-opening device according to certain other embodiments of the present disclosure. FIG. 5A illustrates a device 50 wherein housing 52 has a smooth interior wall 60 such that the device is applied to female Luer connector 40 of FIG. 4B by sliding rather than screwing device 50 onto the threads 42 of female Luer connector 40. FIG. 5B shows a device 50 having a lining 62 of an elastomeric material located on the wall of chamber 53 and sized such that the sleeve 62 contacts the threads 42 or external wall of body 41 such that the device 50 is removably retained on female Luer connector 40. Lining 62 may be a coating on the wall of chamber 53 or a separate sleeve that is inserted into the chamber 53. FIG. 4C discloses a configuration wherein the matrix 56 is formed such that a portion 64 of matrix 56 coats a portion of the inner wall of chamber 53 and a second portion 65 coats a portion of finger 58. In this example, matrix 56 does not cover the tip of finger 58 although other configurations may cover the entire surface of finger 58. FIG. 5D illustrates a configuration wherein the matrix 56 has a portion 66 that coats a portion of the smooth inner wall of chamber 53 and a portion 68 that coats a portion of finger 58 wherein finger 58 is undercut where portion 68 terminates.

Figure 6:
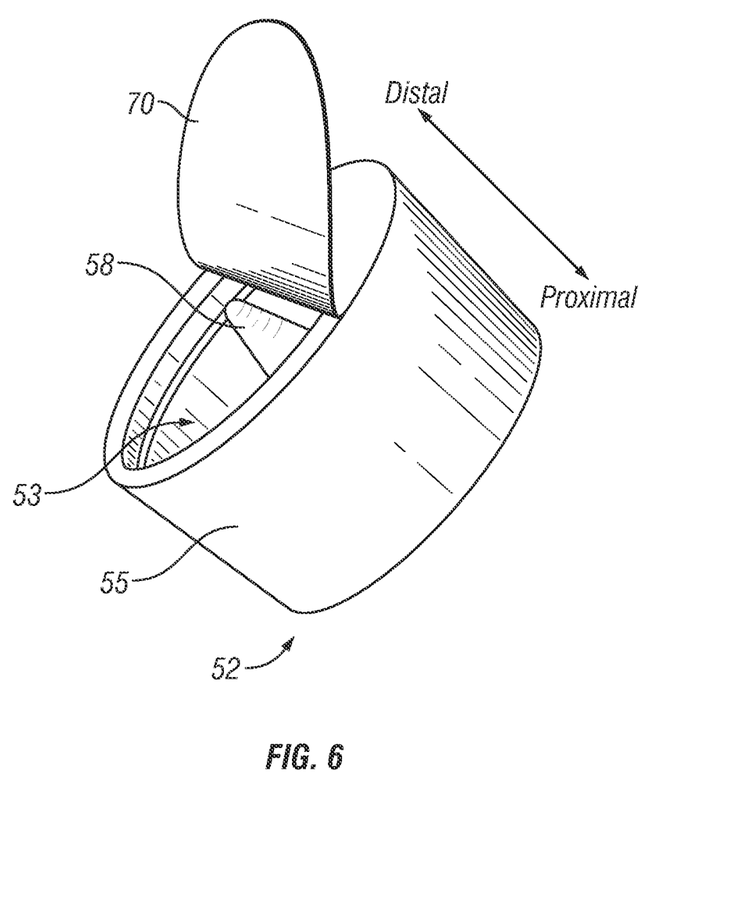
FIG. 6 illustrates a disinfecting and pre-opening device configured as a separate item according to certain aspects of the present disclosure.

FIG. 6 illustrates a disinfecting and pre-opening device configured as a separate item according to certain embodiments of the present disclosure. Certain features depicted in FIG. 6 can be employed with any of the embodiments of FIGS. 4a-4B and FIGS. 5A-5D. In this example, the circumferential sidewall 55 is a tapered cylinder. In certain embodiments, the circumferential sidewall 55 may be configured as a square, a hexagon, or other shape with or without a taper. There is a proximal wall (not visible in this view) that is attached and sealed to the circumferential side wall 55 around the entire circumference of the circumferential side wall 55 along the proximal edge of the circumferential side wall 55, forming a sealed cup-like structure. The housing 52 may be molded in a single piece from a plastic, such as polypropylene or styrene, or other suitable material. Chamber 53 contains a disinfectant that may be carried in a liquid-absorbing matrix (not shown). A lid 70 is sealed across the distal opening of chamber 53. Lid 70 comprises a low permeability material such as aluminum foil and is sealed to housing 52 to form a vapor and liquid barrier to prevent leakage or evaporation of the disinfectant liquid that is contained in chamber 53. The lid 70 is further configured to overhang the edge of housing 52 or, alternately, have a tab that projects beyond the rim of housing 52 such that the lid 70 can easily be peeled off the housing 52. Lid 70 may also have a second tab or flap (not shown) that is folded over and bonded to the external surface of the circumferential side wall 55 such that the lid 70 is not detached from the housing 52 after the lid 70 is peeled away from the distal edge of the circumferential side wall 55, avoiding the creation of a separate piece of trash. It shall be appreciated by those skilled in the art in view of the subject disclosure that a sealing mechanism other than the peelable lid, such as a snap-fit cover, may be employed without departing from the scope of the subject disclosure. An elongated finger 58 is located within chamber 53 and, in this example, having a height such that the tip of the elongated finger is within the chamber 53 so that lid 70 is not in contact with finger 58.

Figure 7:
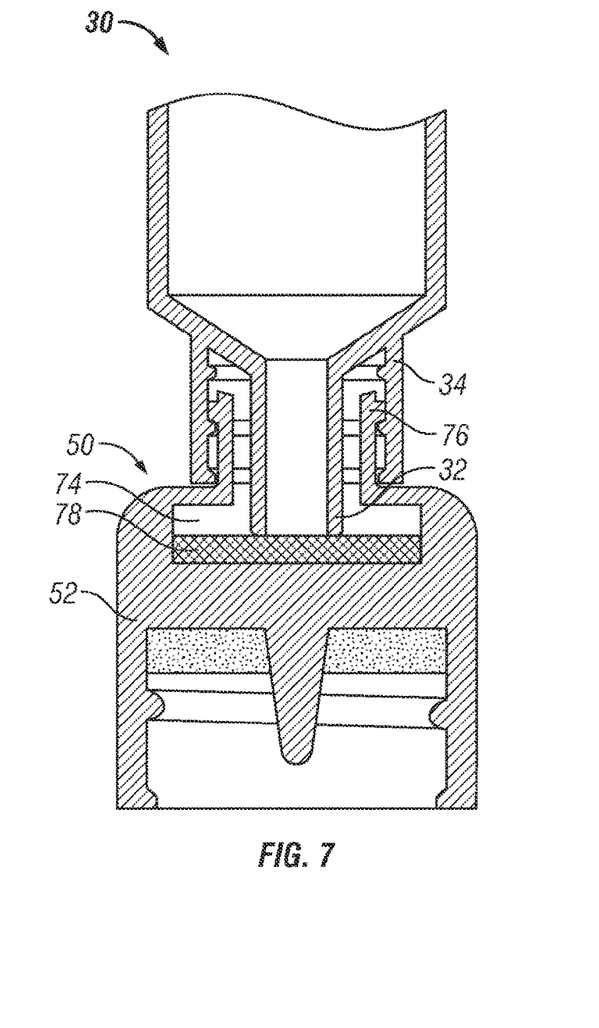
FIG. 7 illustrates a disinfecting and pre-opening device configured to incorporate a Luer cap according to certain embodiments of the present disclosure.

FIG. 7 illustrates a disinfecting and pre-opening device configured to incorporate a Luer cap according to certain aspects of the present disclosure. In this example, the housing 52 further includes a second chamber 74 and a neck 76 sized and configured to engage the threads 34 of male Luer connector 30. In certain embodiments, device 50 is attached to the male Luer connector 30 as delivered to the user and is therefore assured of being at hand at the time of use. In certain embodiments, device 50 incorporates a sealing layer 78 which seals against Luer tip 32. This configuration is advantageous in that it protects the interior of male Luer connector 30 from contamination prior to use. In certain embodiments, sealing layer 78 may comprise an absorbent material and a disinfectant. Alternate configurations adapted for connection to other types of connectors in this same manner will be apparent to those of ordinary skill in the art without departing from the scope of the subject disclosure.

Figure 8A:
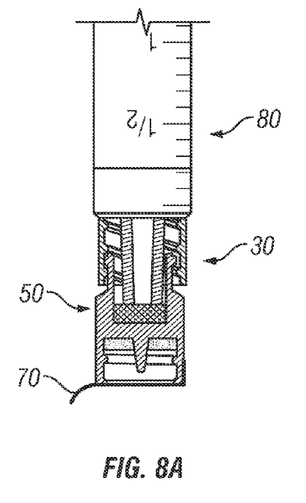
FIGS. 8A-8D depict an example sequence of use of a disinfecting and pre-opening device according to certain embodiments of the present disclosure.
Figure 8B:
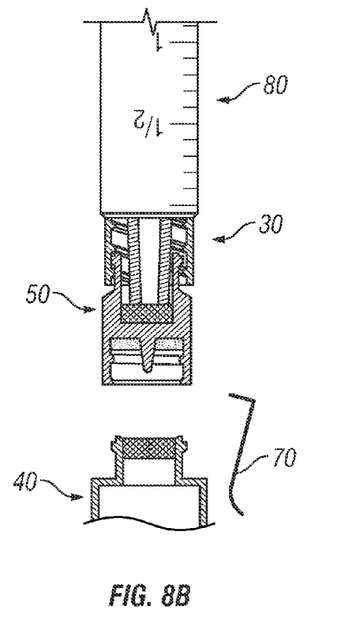
Figure 8C:
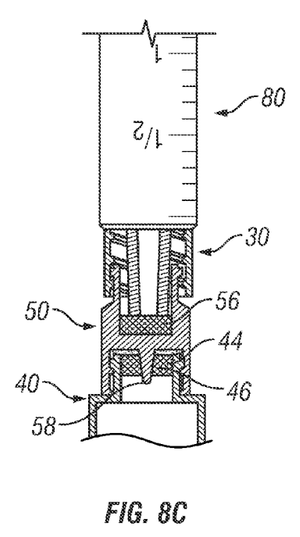
Figure 8D:
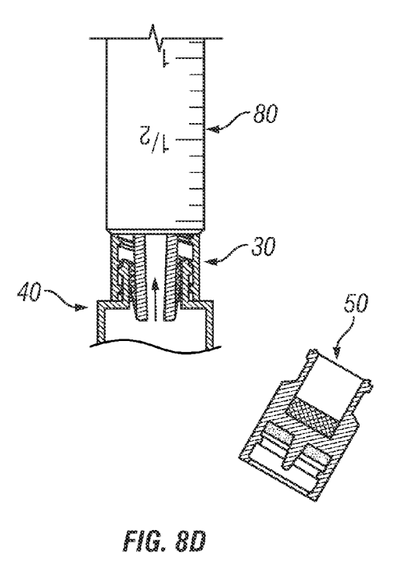

FIGS. 8A-8D depict an example sequence of use of a disinfecting and pre-opening device according to certain aspects of the present disclosure. FIG. 8A illustrates a syringe 80 having a device 50, including a peelable lid 70, attached to the male Luer connector 30. The device 50 is the embodiment depicted in FIG. 7. This is representative of how a syringe may be delivered and stocked in a care unit. Other types of fluid containers, infusion sets, tubing, etc. may be substituted in place of the syringe. FIG. 8B illustrates the first step of entirely removing the lid 70 at the time to connect syringe 30 to a female Luer connector 40. An alternate process would be to only peel back lid 70 without detaching lid 70 from device 50. FIG. 8C illustrates device 50 connected to female Luer connector 30 with matrix 56 in contact with septum 44 and finger 58 penetrating through slit 46. FIG. 8D shows the final step wherein the device 50 has been detached from female Luer connector 40 and then removed from syringe 80 and discarded. The male Luer connector 30 of syringe 80 has now been connected to female Luer connector 30 with a fluid path established from syringe 80 to the container attached to female Luer connector 40.

Figure 9:
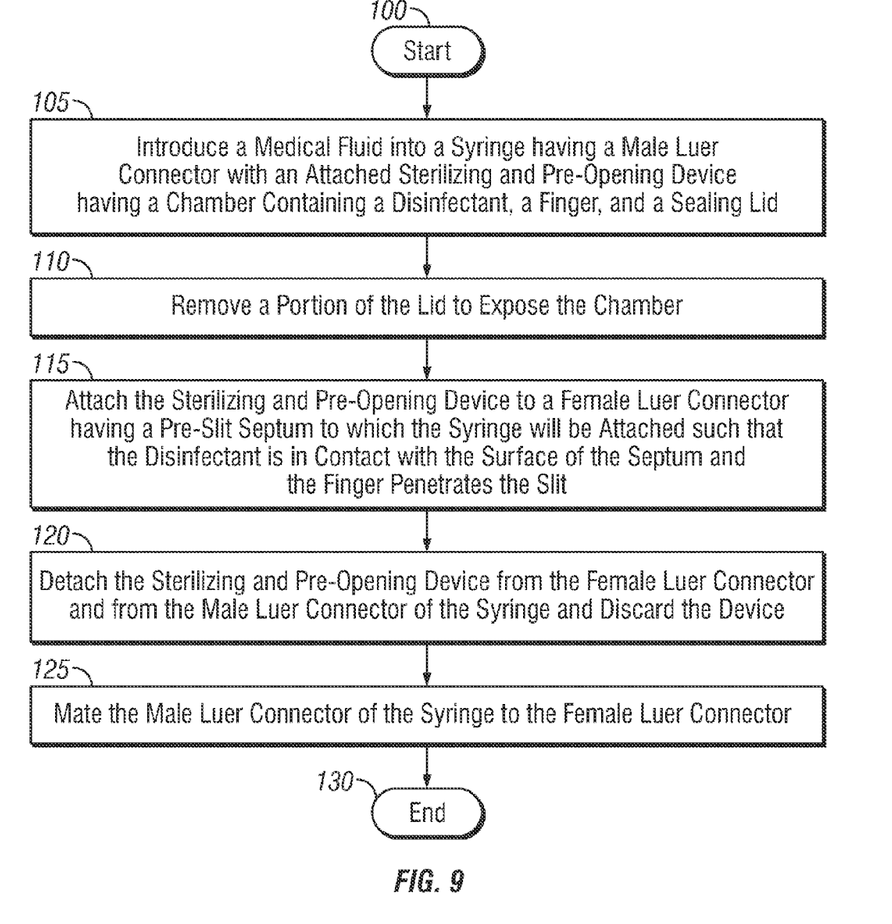
FIG. 9 is a flow chart that illustrates an exemplary method of using a disinfecting and pre-opening device according to certain embodiments of the present disclosure.

FIG. 9 is a flow chart that illustrates an example method of using a disinfecting and pre-opening device according to certain aspects of the present disclosure. This example is drawn to a scenario having a nurse who wishes to administer a medical fluid to a patient using a syringe to introduce the fluid to an intravenous set having an access port having a needleless female Luer connector having a pre-slit septum. Starting at step 100, the nurse selects a syringe having a male Luer connector with an attached disinfecting and pre-opening device of the type illustrated in FIG. 8A and, in step 105, fills the syringe with the medical fluid. Alternately, the nurse could fill a syringe and collect a separate disinfecting and pre-opening device. In step 110, the nurse removes the lid from the disinfecting and pre-opening device, exposing the disinfectant-filled matrix and the pre-opening finger. In step 115, the nurse attaches the disinfecting and pre-opening device to the female Luer connector of, in this example, the access port of the IV set and tightens the disinfecting and pre-opening device onto the female Luer connector until the disinfectant-filled matrix comes into contact with the septum and the finger penetrates the slit. The nurse then, in step 120, detaches the disinfecting and pre-opening device from the female Luer connector and also removes the disinfecting and pre-opening device from the syringe and discards the disinfecting and pre-opening device. The nurse then attached the male Luer connector of the syringe to the female Luer connector of the access port as described in step 125. This completes the process, indicated by step 130, and the system is configured to administer the medical fluid to the patient.

In summary, a disinfecting and pre-opening device has been disclosed that is suitable for use with female Luer connectors having a pre-slit septum. The device applies a disinfectant to the exposed surface of a female needleless connector and pre-opens the slit in the septum. The application of a disinfectant reduces the chance of a bacteria or other microbe being carried by the fluid passing through the female Luer connector into the bloodstream of a patient. The pre-opening of the slit reduces the chance of a male Luer connector not properly mating with the female Luer connector due to cross-linking of the septum across the slit or a lack of lubrication within the slit. As resolution of a problem in mating Luer connectors may require replacement of the entire IV set, which introduces a risk of infection, both the application of disinfectant and the pre-opening of the slit increase the safety of the patient by reducing the chance of infection. Additionally, the disinfecting and pre-opening device is in a convenient sealed package that can be carried by the nurse or provided as an attachment to the syringe or other item having a male Luer connector, reducing the chance that the nurse will not have the proper supplies at hand to sterilize the female Luer connector.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects.

Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The term "slit" is used to indicate a separation of a flexible barrier that allows an elongated element to pass through the flexible barrier by widening the separation generally without further cutting or puncture of the flexible barrier. In some cases, the slit may not traverse the entire thickness of the flexible barrier, with the remaining portion of the thickness left intact to present a complete seal prior to the first insertion of an elongated element. The two sides of the slit may be in intimate contact and form a liquid-tight seal when the slit is in an undeformed condition. The slit may be a single linear cut, in plan view, or may have a more complex form such as two cuts in the form of an "X" or a plurality of cuts on a common center at angles to each other.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Concepts

This writing has disclosed at least the following concepts.

Concept 1. A device for use with a female needleless connector having a proximal end, comprising:
  a housing comprising a chamber having a proximal wall, a continuous side wall coupled to the proximal wall, and a distal opening that is configured to fit over the proximal end of the female needleless connector;
  a fluid-absorbing matrix disposed within the chamber;
  a disinfectant disposed within the fluid-absorbing matrix;
  a solid elongated finger attached to the proximal wall of the housing and disposed within the chamber such that the elongated finger opens the fluid path through the female needleless connector when the distal opening of the housing is placed adjacent to the proximal end of the female needleless connector and the device is advanced in the distal direction; and
  a lining on a portion of an internal surface of the chamber and configured to create a removable interference fit with an external surface of the female needleless connector.

Concept 2. The device of Concept 1, wherein: the female needleless connector comprises a septum located at the proximal end of the female needleless connector, the septum having a pre-cut slit; and
  the elongated finger substantially penetrates the septum through the pre-cut slit when the distal opening of the device is placed proximally adjacent to the septum and the device is advanced in the distal direction.

Concept 3. The device of Concept 1, wherein: the female needleless connector comprises a piston that is surrounded by a housing; and
  the elongated finger displaces the piston relative to the housing when the distal opening of the device is placed adjacent to the proximal end of the female needleless connector and the device is advanced in the distal direction.

Concept 4. The device of Concept 1, further comprising a vapor bather lid removably sealed across the distal opening of the chamber.

Concept 5. The device of Concept 4, wherein the portion of the chamber sealed by the vapor barrier lid is sterile.

Concept 6. The device of Concept 1, wherein the matrix is disposed on a proximal wall of the chamber.

Concept 7. The device of Concept 6, wherein the matrix is further disposed on a portion of a sidewall adjacent to the proximal wall of the chamber.

Concept 8. The device of Concept 6, wherein the matrix is further disposed on a portion of the elongated finger.

Concept 9. The device of Concept 1, wherein the housing further comprises a second chamber and a neck that is sized and configured to removably couple to a male needleless connector.

Concept 10. The device of Concept 1, wherein the female needleless connector comprises a housing and an external thread formed on an external circumferential surface of the housing, and the device further comprising a thread formed on an internal surface of the chamber and configured to engage the external thread of the female needleless connector.

Concept 11. The device of Concept 1, wherein the female needleless connector is a Luer fitting.

Concept 12. A device for use with a female needleless connector having a proximal end, comprising:
a housing comprising (i) a first chamber having a proximal wall, a continuous side wall coupled to the proximal wall, and a distal opening that is configured to fit over the proximal end of the female needleless connector, and (ii) a second chamber and a neck that is sized and configured to removably couple to a male needleless connector;
a fluid-absorbing matrix disposed within the first chamber;
a disinfectant disposed within the fluid-absorbing matrix;
a solid elongated finger attached to the proximal wall of the housing and disposed within the first chamber such that the elongated finger opens the fluid path through the female needleless connector when the distal opening of the housing is placed adjacent to the proximal end of the female needleless connector and the device is advanced in the distal direction.

Concept 13. The device of Concept 12, wherein: the female needleless connector comprises a septum located at the proximal end of the female needleless connector, the septum having a pre-cut slit; and
the elongated finger substantially penetrates the septum through the pre-cut slit when the distal opening of the device is placed proximally adjacent to the septum and the device is advanced in the distal direction.

Concept 14. The device of Concept 12, wherein: the female needleless connector comprises a piston that is surrounded by a housing; and
the elongated finger displaces the piston relative to the housing when the distal opening of the device is placed adjacent to the proximal end of the female needleless connector and the device is advanced in the distal direction.

Concept 15. The device of claim 12, further comprising a vapor bather lid removably sealed across the distal opening of the chamber.

Concept 16. The device of Concept 15, wherein the portion of the chamber sealed by the vapor barrier lid is sterile.

Concept 17. The device of Concept 12, wherein the matrix is disposed on a proximal wall of the chamber.

Concept 18. The device of Concept 17, wherein the matrix is further disposed on a portion of a sidewall adjacent to the proximal wall of the chamber.

Concept 19. The device of Concept 17, wherein the matrix is further disposed on a portion of the elongated finger.

Concept 20. The device of Concept 12, wherein the female needleless connector comprises a housing and an external thread formed on an external circumferential surface of the housing, and the device further comprising a thread formed on an internal surface of the chamber and configured to engage the external thread of the female needleless connector.

Concept 21. The device of Concept 12, further comprising a lining on a portion of an internal surface of the chamber and configured to create a removable interference fit with an external surface of the female needleless connector.

Concept 22. The device of Concept 12, wherein the female needleless connector is a Luer fitting.

What is claimed is:

1. A device for use with a female needleless connector, the device comprising:
a housing comprising a chamber having a proximal wall, a continuous side wall coupled to the proximal wall, and a distal opening that is configured to fit over a proximal end of the female needleless connector;
a solid elongated finger attached to the proximal wall of the housing and disposed within the chamber such that the elongated finger extends into and opens a fluid path through the female needleless connector when the distal opening of the housing is placed adjacent to the proximal end of the female needleless connector and the housing is distally advanced ; and
a lining on a portion of an internal surface of the chamber and configured to create a removable interference fit with an external surface of the female needleless connector.

2. The device of claim 1, wherein:
the female needleless connector comprises a septum located at the proximal end of the female needleless connector, the septum having a pre-cut slit; and
the elongated finger substantially penetrates the septum through the pre-cut slit when the distal opening of the device is placed proximally adjacent to the septum and the device is advanced in the distal direction.

3. The device of claim 1, wherein:
the female needleless connector comprises a piston that is surrounded by a housing; and
the elongated finger displaces the piston relative to the housing when the distal opening of the device is placed adjacent to the proximal end of the female needleless connector and the device is advanced in the distal direction.

4. The device of claim 1, further comprising a vapor barrier lid removably sealed across the distal opening of the chamber.

5. The device of claim 4, wherein the portion of the chamber sealed by the vapor barrier lid is sterile.

6. The device of claim 1, further comprising a fluid-absorbing matrix that contains a disinfectant, the matrix disposed within the chamber.

7. The device of claim 1, wherein the matrix is disposed on a proximal wall of the chamber.

8. The device of claim 7, wherein the matrix is further disposed on a portion of a sidewall adjacent to the proximal wall of the chamber.

9. The device of claim 7, wherein the matrix is further disposed on a portion of the elongated finger.

10. The device of claim 1, wherein the housing further comprises a second chamber and a neck that is sized and configured to removably couple to a male needleless connector.

11. The device of claim 1, further comprising a fluid-absorbing matrix that contains a disinfectant, the matrix disposed within the chamber.

12. The device of claim 11, wherein the matrix is disposed on a proximal wall of the chamber.

13. The device of claim 12, wherein the matrix is further disposed on a portion of a sidewall adjacent to the proximal wall of the chamber.

14. The device of claim 12, wherein the matrix is further disposed on a portion of the elongated finger.

15. A device for use with a female needleless connector, the device comprising:
a housing comprising (i) a first chamber having a proximal wall, a continuous side wall coupled to the proximal wall, and a distal opening that is configured to fit over a proximal end of the female needleless connector, and (ii) a second chamber and a neck that is sized and configured to removably couple to a male needleless connector;

a solid elongated finger attached to the proximal wall of the housing and disposed within the first chamber such that the elongated finger opens a fluid path through the female needleless connector when the distal opening of the housing is advanced distally beyond the proximal end of the female needleless connector.

16. The device of claim 15, wherein:

the female needleless connector comprises a septum located at the proximal end of the female needleless connector, the septum having a pre-cut slit; and the elongated finger substantially penetrates the septum through the pre-cut slit when the distal opening of the device is placed proximally adjacent to the septum and the device is advanced in the distal direction.

17. The device of claim 15, wherein:

the female needleless connector comprises a piston that is surrounded by a housing; and the elongated finger displaces the piston relative to the housing when the distal opening of the device is placed adjacent to the proximal end of the female needleless connector and the device is advanced in the distal direction.

18. The device of claim 15, further comprising a vapor barrier lid removably sealed across the distal opening of the chamber.

19. The device of claim 15, further comprising a lining on a portion of an internal surface of the chamber and configured to create a removable interference fit with an external surface of the female needleless connector.

20. The device of claim 15, wherein the female needleless connector is a Luer fitting.

\* \* \* \* \*